United States Patent [19]

Fisher et al.

[11] Patent Number: 4,704,397

[45] Date of Patent: Nov. 3, 1987

[54] PHARMACEUTICAL SALTS OF 4-(9-ACRIDINYL-AMINO) METHANESULFON-M-ANISIDIDE

[75] Inventors: James R. Fisher, Royal Oak; Charles P. Kulier, Holland, both of Mich.

[73] Assignee: Warner-Lambert Company, Morris Plains, N.J.

[21] Appl. No.: 302,944

[22] Filed: Sep. 16, 1981

Related U.S. Application Data

[63] Continuation-in-part of Ser. No. 129,503, Mar. 11, 1980, abandoned.

[51] Int. Cl.$^4$ ................. C07D 219/10; A61K 31/435
[52] U.S. Cl. ...................................... 514/297; 546/106
[58] Field of Search ...................... 546/106; 424/257; 514/297

[56] References Cited

PUBLICATIONS

Legha, et al., Annals of Internal Medicine, vol. 93, pp. 17–21 (1980).
McCredie, et al., AACR, abstract C-571, (1981).
Cain, et al., Europe J. Cancer, vol. 10, pp. 539–549 (1974).
Cain, et al., J. Med. Chem, vol. 15, pp. 611–615 (1972).
Cain, et al., J. Med. Chem., vol. 18, pp. 1110–1117 (1975).
Cain, et al., J. Med. Chem., vol. 19, pp. 772–777 (1976).
Cain, et al., J. Med. Chem., vol. 19, pp. 1409–1416 (1976).
Cain, et al., J. Med. Chem., vol. 20, pp. 987–996 (1977).
Denny, et al., J. Med. Chem., vol. 21, pp. 5–10 (1978).
Cain, et al., Molecular Pharmacology, vol. 12, pp. 1027–1035 (1976).
Dupont, J., et al., AACR, abstract C-562 (1981).
Goldsmith, et al., Cancer Clinical Trials, vol. 3, pp. 197–202 (1980).
Kahn, et al., AACR, abstract C-614, (1981).
Land, et al., AACR, abstract C-279, (1981).
Lawrence, et al., AACR, abstract C-471, (1980).
Legha, et al., AACR, Abstract C-518 (1979).

*Primary Examiner*—Alan L. Rotman
*Attorney, Agent, or Firm*—Pennie & Edmonds

[57] ABSTRACT

Pharmaceutical salts of 4'-(9-acridinylamino)--methanesulfon-m-anisidide, methods for their preparation and use of said salts in the form of pharmaceutical compositions as antineoplastic agents.

21 Claims, No Drawings

PHARMACEUTICAL SALTS OF 4-(9-ACRIDINYL-AMINO) METHANESULFON-M-ANISIDIDE

CROSS-REFERENCE TO RELATED APPLICATION

This application is a continuation-in-part of copending U.S. application Ser. No. 129,503, filed Mar. 11, 1980, now abandoned.

SUMMARY AND DETAILED DESCRIPTION

The present invention relates to pharmaceutically acceptable acid-addition salts of 4'-(9-acridinylamino)methanesulfon-m-anisidide (m-AMSA), which has the structure

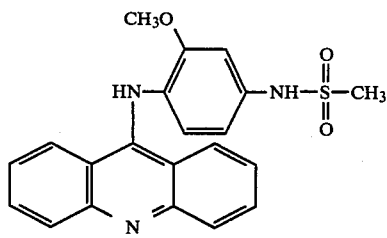

wherein said salts have a relatively high degree of solubility in water and remain in solution for a sufficient period of time to permit the solution to be introduced into a mammal. The term "solution" is defined in this invention as a material which is in a liquid fluid state capable of almost completely passing through about a 0.22μ millipore filter. Certain of the salts do form true solutions; however, this may not always be the case. More specifically, the invention relates to pharmaceutically acceptable acid-addition salts of the formula m-AMSA·X wherein X is an acid having a total of from three to six carbon atoms, two to five hydroxy groups and an acidic group which may be a —$CO_2H$ group or a —$OPO_3H_2$ group with the proviso that when the total number of carbon atoms is three or four, the acidic group is $OPO_3H_2$.

The compound X of the formula m-AMSA·X, may be in the D, L or a racemic form. In addition, the salt m-AMSA·X may exist in a solvated form. All of the foregoing forms are intended to be encompassed by the formula m-AMSA·X.

The preferred acids represented by X are D-gluconic acid, D-glucuronic acid, D-galacturonic acid and β-glycerophosphoric acid which give rise to 4'-(9-acridinylamino)methanesulfon-m-anisidide D-gluconate, 4'-(9-acridinylamino)methanesulfon-m-anisidide D-glucuronate, 4'-(9-acridinylamino)methanesulfon-m-anisidide D-galacturonate, and 4'-(9-acridinylamino)methanesulfon-m-anisidide β-glycerophosphate, respectively.

The present invention also relates to methods for preparing said salts, pharmaceutical compositions utilizing said salts and methods of treating mammals having certain viral or microbial infections, cancer or a tumor with said salts, preferably in the form of the disclosed pharmaceutical compositions.

The compound 4'-(9-acridinylamino)methanesulfon-m-anisidide, generally referred to as m-AMSA, has been found to have a high degree of activity in treating mammals in studies using mice:

"The Experimental Antitumour Properties of Three Congeners of the Acridylmethanesulphonanilide (AMSA) Series", B. F. Cain and G. J. Atwell, Europe. J. Cancer, Vol. 10, pp. 539–549. Pergamon Press (1974);

"Potential Antitumor Agents. 16. 4'-(Acridin-9-ylamino)methanesulfonanilides", Bruce F. Cain, Graham J. Atwell and William A. Denny, Journal of Medicinal Chemistry, Vol. 18, pp. 1110–1117 (1975);

"Structure-Activity Relationships for Thiolytic Cleavage Rates of Antitumor Drugs in the 4'-(9-Acridinylamino)methanesulfonanilide Series", Bruce F. Cain, William Robert Wilson and Bruce C. Baguley, Molecular Pharmacology, Vol. 12, pp. 1027–1035 (1976);

"Potential Antitumor Agents. 17. 9-Anilino-10-methylacridinium Salts", Bruce F. Cain, Graham J. Atwell and William A. Denny, Journal of Medicinal Chemistry, Vol. 19, pp. 772–777 (1976); "Potential Antitumor Agents. 26. Anionic Congeners of the 9-Anilinoacridines", William A. Denny, Graham J. Atwell and Bruce F. Cain, Journal of Medicinal Chemistry, Vol. 21, pp. 5–10 (1978).

The compound m-AMSA is generally prepared by coupling 9-chloroacridine to 4'-aminomethanesulfon-m-anisidide under acid-catalyzed conditions which is described in the following references:

"Potential Antitumor Agents. 12. 9-Anilinoacridines", G. J. Atwell, B. F. Cain and R. N. Seelye, Journal of Medicinal Chemistry, Vol. 15, pp. 611–615 (1972);

"The Experimental Antitumour Properties of Three Congeners of the Acridylmethanesulphonanilide (AMSA) Series", B. F. Cain and G. J. Atwell, Europ. J. Cancer, Vol. 10, pp. 539–549. Pergamon Press (1974);

"Potential Antitumor Agents. 16. 4'-(Acridin-9-ylamino)methanesulfonanilides", Bruce F. Cain, Graham J. Atwell and William A. Denny, Journal of Medicinal Chemistry, Vol. 18, pp. 1110–1117 (1975);

"Potential Antitumor Agents. 17. 9-Anilino-10-methylacridinium Salts", Bruce F. Cain, Graham J. Atwell and William A. Denny, Journal of Medicinal Chemistry, Vol. 19, pp. 772–777 (1976);

"Potential Antitumor Agents. 20. Structure-Activity-Site Relationships for the 4'-(9-Acridinylamino)alkanesulfonanilides", Bruce F. Cain and Graham J. Atwell, Journal of Medicinal Chemistry, Vol. 19, pp. 1409–1416 (1976);

"Potential Antitumor Agents. 23. 4'-(9-Acridinylamino) alkanesulfonanilide Congeners Bearing Hydrophilic Functionality", Bruce F. Cain, Graham J. Atwell and William A. Denny, Journal of Medicinal Chemistry, Vol. 20, pp. 987–996 (1977).

which are incorporated by reference.

Unfortunately, m-AMSA is a compound which is not water soluble. It also has been found that the salts of m-AMSA, such as the hydrochloride salt, are also of a low order of solubility in water (see Table I). If the compound is to be administered parenterally, a solution containing the compound must be prepared. At present, solutions employing dimethylacetamide as the solvent have been tried; however, the toxicity associated with this solvent makes this approach very undesirable. A host of undesirable side reactions are associated with the use of significant quantities of dimethylacetamide, see Cancer Chemotherapy Reports, No. 16, February 1962, 477–485. In addition, the dimethylacetamide is a potent solvent which presents problems as relates to the tubing and plastic syringes used when administering or storing the solution.

It has been found that certain acids when reacted with m-AMSA give salts having high degrees of water solubility. The salts of the present invention allow one to prepare solutions of m-AMSA without the aid of dimethylacetamide. Depending upon the salt, concentration and temperature, standing may result in certain of the solutions of salts forming gels. However, a salt need only remain in solution for a period long enough for it to be administered to a patient. The stability of aqueous solutions of certain preferred compounds is given in Table II.

TABLE I

| Relative Solubility of m-AMSA Salts[a],[b] | |
|---|---|
| Acid | Rel. Solubility as Comp. to H$_2$O |
| Galacturonic | 6133 |
| Glucose-6-Phosphoric | 3785 |
| Gluconic | 2815 |
| Ascorbic | 1213 |
| β-Glycerophosphoric | 1085 |

TABLE I-continued

| Relative Solubility of m-AMSA Salts[a],[b] | |
|---|---|
| Acid | Rel. Solubility as Comp. to H$_2$O |
| Glucuronic | 923 |
| Lactic | 890 |
| Glyceric | 555 |
| Citric | 438 |
| Acetic | 234 |
| Propionic | 225 |
| Gallic | 225 |
| Isethionic | 213 |
| Malonic | 192 |
| D,L-Malic | 165 |
| Succinic | 154 |
| d-Tartaric | 138 |
| Glutaric | 102 |
| Mucic | 33 |
| Phosphoric | 29 |
| Salicylic | 18 |
| Glycolic | 18 |
| Benzoic | 10 |
| Methane-Sulfonic | 7.5 |
| Gentisic | 7.5 |
| Sulfuric | 6 |
| Nitric | 3 |
| Sulfamic | 2.8 |
| Hydrochloric | 1.2 |
| Water | 1 |

[a]After solution is achieved, certain solutions upon standing set up like gels. The fact that on standing gels form in certain instances is not reflected in the table.
[b]The values were obtained by adding m-AMSA to 0.1 M aqueous solutions, except gallic acid (0.05 M), mucic acid (0.01 M), salicylic acid (0.015 M), benzoic acid (0.015 M) and gentisic (0.03 M).

TABLE II

| Stability of Preferred m-AMSA Salts | | | |
|---|---|---|---|
| m-AMSA Salt | m-AMSA Concentration mg/ml | Temperature °C. | Results |
| gluconate | 5.2 | room temperature | (a) after four days - fluid and clear to tyndall light. (b) after three weeks - fluid and clear to ordinary light, haze by tyndall light. |
| gluconate | 5.2 | 5° | (a) after four days - solution gelled. |
| gluconate | 7.4 | room temperature | (a) after three days - fluid and clear to tyndall light. (b) after three weeks - fluid and clear to ordinary light, haze by tyndall light. |
| gluconate | 7.4 | 5° | (a) after three days - solution gelled. |
| gluconate | 10 | room temperature | (a) after 18 hours - fluid and clear to tyndall light. (b) after 18 days - clear to ordinary light, haze by tyndall light. |
| gluconate | 10 | 5° | (a) after 18 hours - solution gelled. (b) after 18 days - solution gelled* with slight flocculant precipitate. |
| glucuronate | 4.97 | room temperature | (a) after 18 days - hazy to tyndall light and some particles. |
| glucuronate | 4.97 | 5° | (a) after 18 days - solution gelled but liquifies on warming to room temperature with stirring (haze to tyndall light and slight precipitate). |
| β-glycerophosphate | 7.5 | room temperature | (a) after three days - fluid and clear to tyndall light. (b) after three weeks - solution gelled but became fluid on shaking (haze to tyndall light). |
| β-glycerophosphate | 7.5 | 5° | (a) after three days - gelled (warming to room temperature and shaking gave solution clear |

TABLE II-continued

Stability of Preferred m-AMSA Salts

| m-AMSA Salt | m-AMSA Concentration mg/ml | Temperature °C. | Results |
|---|---|---|---|
| | | | by tyndall light). (b) after three weeks - gelled (warming to room temperature and shaking gave solution hazy to tyndall light). |

*all foregoing gluconate solutions of lower concentration that gelled at 5° C. could be returned to a fluid state by warming to room temperature and shaking, at 10 mg/ml this could not be achieved after storing at 5° C.

It is also noted that solubility is enhanced by the presence of an excess of an acid of the formula X' wherein X' is an acid having a total of from three to six carbon atoms, two to five hydroxy groups and an acidic group which may be a —$CO_2H$ group or a —$OPO_3H_2$ group with the proviso that when the total number of carbon atoms is three or four, the acidic group is $OPO_3H_2$.

The acid X' may or may not be the same as the acid used in forming the salt of m-AMSA. Generally, the same acid is employed to form the salt of m-AMSA and supply the excess acid, since it is more convenient to use this approach to prepare the m-AMSA salt with excess acid (X and X' are the same in this instance). The quantity of excess acid used, when compared to the m-AMSA salt on a molar basis, is about 0.2 moles to about 10.0 moles per mole of m-AMSA salt, preferably approximately 1.0 moles to approximately 6.0 moles.

The salts are prepared from m-AMSA base and the acid in an inert solvent. Although up to 10% molar excess of either reagent may be employed, equimolar proportions of m-AMSA base and the acid are preferred.

The m-AMSA base and the acid are dissolved in dimethylformamide, dimethylacetamide, methanol, anhydrous ethanol, 95% ethanol, isopropanol or combinations of the solvents at 35° to 100° C. After filtration of the solution, the salt is precipitated by addition of another solvent such as anhydrous ethanol, isopropanol, anhydrous diethyl ether or ethyl acetate and/or chilling at 5° to −20° C. for 2 to 24 hours. The preferred method is to dissolve the m-AMSA base and acid in anhydrous ethanol and dimethylformamide at 70°-100°, in boiling anhydrous ethanol or in boiling methanol. The solution is filtered and the salt separated from the filtrate by the following procedures. The dimethylformamide-anhydrous ethanol solution (about 70° C.) is diluted with anhydrous ethanol; the anhydrous ethanol and the methanol solutions at 30°-35° C. are diluted with diethyl ether. The product is further precipitated by chilling the filtrates at 5° to −20° C. for 16-24 hours. After collecting the product it is dried under reduced pressure at 50°-60° C.

The compounds of the present invention are useful in treating certain viral infections, namely those caused by Avian myeloblastoma or vaccinia virus or certain bacterial infections, namely those caused by Salmonella typhimurium bacteria.

The use of m-AMSA in treating leukemia is reported in

1. Dupont, J., et al.—a Phase II trial of m-AMSA in acute leukemia. AACR (abstract C-562) 1981.
2. Goldsmith, M. A., et al.—Phase I study of m-AMSA in patients with solid tumors and leukemias. *Cancer Clinical Trials* 3:197-102, 1980.
3. Kahn, S. B., et al.—Combined m-AMSA (NSC 2499) and 5-azacytidine (AZA) in the therapy of relapsed acute leukemia and the accelerated phase of chronic myeloid leukemia (CML) AACR (abstract C-614) 1981.
4. Land, V. J., et al.—Efficacy and toxicity of methanesulfon-m-anisidine, 4'-(9-acridinylamino) 24992) (m-AMSA) in advanced childhood leukemia. *ACCR* (Abstract C-471) 1980.
5. Lawrence, H. J., et al.—m-AMSA: a promising new agent in refractory acute leukemia. *AACR* (abstract C-471) 1980.
6. Legha, S. S., et al.—Early clinical evaluation of acridinylaminomethanesulfon-m-anisidide (AMSA) in patients with advanced breast cancer and acute leukemia. *AACR* (abstract C-518) 1979.
7. Legha, S. S., et al.—4'-(9-acridinylamino)methanesulfon-m-anisidide (AMSA): a new drug effective in the treatment of adult acute leukemia. *Annals of Internal Medicine*, 1980 93 (Part 1): 17-21.
8. McCredie, K. B., et al.—Use of a 4'-(9-acridinylamino)methanesulfon-m-anisidide (AMSA), cytosine-arabinoside (Ara-C) vincristine prednisone combination (AMSA-OAP) in poor risk patients in acute leukemia. *AACR* (abstract C-571) 1981;

breast cancer is reported in

1. Buzdar, A. U., et al.—Phase II evaluation of AMSA in combination with peptichemio in metastic breast cancer resistant to conventional chemotherapy. *AACR* (abstract 724) 1980.
2. Legha, S. S., et al.—Phase II study of 4'-(9-acridinylamino)methanesulfon-m-anisidide (AMSA) in metastatic breast cancer. *Cancer Treatment Reports* Vol. 63, No. 11-12, November/December 1979.
3. Samal, B. A., et al.—m-AMSA for treatment of disseminated breast cancer. *AACR* (abstract 175) 1980;

and lymphoma is reported in

1. Cabanillas, F., et al.—Phase II study of AMSA (acridinylaminomethanesulfon-m-anisidide) in lymphoproliferative disorders. *AACR* (Abstract 624) 1980.
2. Cabanillas, F., et al.—initial experience with AMSA as single agent treatment against malignant lympoproliferative disorders. *Blood*, vol. 57, No. 3 (March), 1981.
3. Warrell, Jr., R. P., et al.—Phase II trial of 4'-(9-acridinylamino)methanesulfon-m-anisidide (AMSA) in the treatment of advanced non-Hodgkin's lymphoma. *Cancer Treatment Reports* Vol. 64, No. 10-11, October/November 1980.

These papers are incorporated by reference.

The preferred route of administration is intravenous and the dose generally employed is from about 20 mg to about 500 mg/m$^2$ of body surface per day for one to five days preferably 30 mg to 100 mg/m$^2$ per day for about three days. The procedure may be repeated about every three weeks.

The compounds of the present invention may also be administered orally in the form of capsules, tablets, syrups, etc., or rectally in the form of suppositories. Generally, higher doses are employed when using these routes, especially orally. Thus, when employing these routes about 20 mg to about 1.0 g/m$^2$ of body surface per day for from one to five days, preferably 50 mg to 800 mg/m$^2$ per day for about three days is used.

The compounds of the invention, when administered intravenously, are generally dissolved in water, sterifiltered, lyophilized and redissolved at the time of use. Preferably, an excess of acid is present to further improve solubility and minimize the chances of any blockage of the pores during the sterifiltration step. An excess of an acid is less desirable if the sterilization process does not utilize a microfiltration step. The lyophilized material is dissolved in a non-toxic aqueous vehicle prior to administration. The vehicle may contain buffers, materials, to make the resultant solution isotonic, preservatives, etc., which are compatable with the compounds of this invention. Certain ions, such as halide ion, cause precipitation of the hydrohalide salt of m-AMSA and should be avoided.

In addition, the compounds of the present invention are orally administered, for example, with an inert diluent or with an assimilable edible carrier, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 10 and 200 milligrams of active compound.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye, and a flavoring such as cherry or orange flavor. Of course, any material used in preparing any dosage unit form should be pharmaceutically pure and substantially non-toxic in the amounts employed.

Lastly, the compounds of this invention may be administered in the form of a suppository using glycerin, cocoa butter, etc., as a vehicle. In addition to the compounds of the invention, preservatives and/or coloring agents may also be incorporated into the suppository. The enhanced solubility of the m-AMSA salts may also give certain advantages when administered by these routes.

The compounds of this invention may be administered in combination with other antineoplastic agents. The antineoplastics may be derived from the numerous classes of agents; such as: antibiotic derivatives, doxorubicin, mitomycin, actinomycin, etc.; antiestrogen agents, such as tamoxifen; antimetabolites, such as fluorouracil, carmustine, lomustine, methotrexate, mercaptopurine, thioguanine, etc.; cytotoxic agents, such as bleomycin, cyclophosphamide, busulfan, procarbazine, hyroxyurea, etc.; hormones, such as dromostanolone, ethinyl estradiol, megestrol, prednisone, methyltestosterone, chlorotrianisene, testolactone, etc.; nitrogen mustard derivatives, such as melphalan, chlorambucil, methlorethamine, TESPA, etc.; steroids, such as betamethasone, prednisolone, etc., and other miscellaneous agents, such as vinblastine, vincristine, asparaginase, mitotane, cisplatin, etc. When using combinations of two or more neoplastic agents, the dosage of m-AMSA salt may be reduced. The dosage ranges generally employed for the above cited antineoplastics which may be used with m-AMSA are known to the medical profession, see Physicians' Desk Reference, 34th Edition, Medical Economics Co. 1980, which is incorporated by reference.

The invention is illustrated by the following examples.

EXAMPLE 1 m-AMSA D-Gluconate

A solution of 3.93 gm of m-AMSA and 5.15 gm of D-gluconic acid-water solution (38% w/w) in 305 ml of specially denatured 3A anhydrous ethanol at 70°-80° C. is filtered with suction. The filtrate is cooled to 30°-35° C. and 100 ml of anhydrous diethyl ether is added with stirring. After chilling to 0°-5° C. with stirring, the mixture is stored about 16 hours at 5° C. The product is collected, washed with specially denatured 3A anhydrous ethanol and anhydrous diethyl ether (3:1) at 5° C., then with several portions of anhydrous ether and dried under reduced pressure at 50°-55° C. to give 3.95 gm of m-AMSA D-gluconate. The salt obtained by this process retains a small amount (about 1% of ethanol).

EXAMPLE 2 m-AMSA D-Galacturonate

A solution of 3.93 gm of m-AMSA and 2.12 gm of D-galacturonic acid monohydrate in 325 ml of specially denatured 3A anhydrous ethanol at 70°-80° C. is filtered with suction. The filtrate is stirred and chilled to 0°-5° C., then stored at −20° C. for about 16 hours. The product is collected, washed with cold (about −20° C.) specially denatured 3A anhydrous ethanol, then with anhydrous diethyl ether and dried under reduced pressure at 50°-55° C. to give 3.9 gm of m-AMSA D-galacturonate. The salt obtained by this process retains a small amount about 3% of ethanol.

EXAMPLE 3 m-AMSA D-Glucose-6-phosphate

A mixture of 1.1804 gm of m-AMSA and 0.8576 gm of (91%) D-glucose-6-phosphoric acid monohydrate in 19.3 ml of dimethylformamide is heated on a hot plate until a complete solution is obtained at about 100° C. The hot, dark-colored solution is then diluted with an equal volume of warm (65°–70° C.) specially denatured 3A anhydrous ethanol and filtered immediately. Additional warm specially denatured 3A anhydrous ethanol (about 70° C.) is used to rinse the funnel so that a total of 96.5 ml of ethanol is used. The mixture is allowed to cool to about 20°–25° C. with occasional swirling of the flask. The mixture is then cooled for several hours at 3°–5° C. and then for a similar period of time at −18° to −20° C. The solid is collected, washed thoroughly with cold (3°–5° C.) specially denatured 3A anhydrous ethanol, then with anhydrous diethyl ether and dried under reduced pressure at 39°–40° C. to give 1.38 gm of m-AMSA D-glucose-6-phosphate.

EXAMPLE 4 m-AMSA D-Glucuronate

A solution of 3.93 gm of m-AMSA and 2.0 gm of D-glucuronic acid in 325 ml specially denatured anhydrous ethanol at 70°–80° C. is filtered with suction. After cooling to 30°–35° C., 45 ml anhydrous diethyl ether is added with stirring and chilling to 5° C. After chilling about 16 hours at 5° C., the salt is collected, washed with cold (0°–5° C.) specially denatured 3A anhydrous ethanol, then with anhydrous diethyl ether and dried under reduced pressure at 50° C. to give 4.5 gm of m-AMSA D-glucuronate.

EXAMPLE 5 m-AMSA Gluconate Lyophilized Injectable Formulation

|  | per liter |
|---|---|
| 1. m-AMSA Gluconate (11.77 mg/ml*) | 11.77 g |
| 2. Gluconic Acid, 50% Solution | q.s. |
| 3. Celite 521** | 1.5 g |
| 4. Water for Injection, USP q.s. to make | 1000 ml |

*Equivalent to 7.5 mg/ml of m-AMSA plus 3% intentional excess.
**If needed to clarify solution.

Method of Preparation (for 1000 ml)

A. Add sufficient 2 to approximately 900 ml of 4 in a suitable container to adjust the pH of the solution to approximately 2.2.
B. Add 1 slowly with continuous stirring until 1 completely dissolves.
C. Recheck pH and adjust to 2.3–2.7, if needed, with 2.
D. Add a sufficient amount of 4 to make 1000 ml of solution and mix well.
E. If necessary, clarify solution with 3 followed by suitable filtration to remove 3 (Whatman No. 1 filter paper, Millipore AW 19 membrane or equivalent).
F. Sterilize solution by filtration through a previously sterilized membrane (Millipore GS or equivalent) using appropriate prefiltration, if necessary.
G. Aseptically fill into previously sterilized vials (10 ml per vial).
H. Stopper vials loosely with rubber lyophilization stoppers and lyophilize in a suitable lyophilizer, (75 mg m-AMSA per vial).
I. At the conclusion of the lyophilization cycle, stopper and cap vials.

EXAMPLE 6 m-AMSA Gluconate Injectable Formulation

|  | per 1000 vials |
|---|---|
| m-AMSA gluconate (117.7 mg/vial*) | 117.7 g |

*Equivalent to 75 mg of m-AMSA + 3% intentional excess.

Method of Preparation

1. Presterilize the m-AMSA gluconate.
2. Fill into appropriate** (10 ml–20 ml) previously sterilized vials.
3. Stopper and cap vials.

**If 10 vials are used and 10.0 ml of Sterile Water for Injection is used to dissolve the sterile powder, the resulting concentration will be equivalent to 7.5 mg/ml, m-AMSA, as the gluconate. If 20 ml vials are used and 20.0 ml of Sterile Water for Injection is used to dissolve the sterile powder, the resulting concentration will be 3.75 mg/ml.

EXAMPLE 7 m-AMSA Gluconate Oral Formulation

|  | mg/cap | g/1000 caps |
|---|---|---|
| 1. m-AMSA Gluconate | 76.1* mg | 76.2 g |
| 2. Lactose USP Hydrous | 438.8 | 438.8 |
| 3. Polysorbate 80 USP | 5.0 | 5.0 |
| 4. Syloid 74 (silica gel) | 10.0 | 10.0 |
| 5. Alcohol SD 3A Anhydrous | 0.07 ml | 7.0 ml |
|  | 530 mg | 530 g |

*Equivalent to 50 mg m-AMSA Base.

Method of Preparation

A. Dissolve 3 in 5 and add to 4 contained in a suitable blender. Blend thoroughly. Transfer the wet mass onto trays and dry at about 120° F. overnight. Add to 2 and mix well.
B. Screen 1 through a No. 60 screen. Add material from Step A and blend thoroughly. Pass through No. 60 screen and reblend.
C. Fill 530 mg of the powder mixture into No. "0" dark brown opaque hard gelatin capsules.

We claim:

1. The compound, 4'-(9-acridinylamino)methanesulfon-m-anisidide D-gluconate.
2. 4'-(9-acridinylamino)methanesulfon-m-anisidide D-glucuronate.
3. 4'-(9-acridinylamino)methanesulfon-m-anisidide D-galacturonate.
4. A stable, solid, water-soluble composition for reconstitution with water or aqueous vehicle as a stable solution of m-AMSA, said composition comprising a mixture of about one mole of m-AMSA gluconate salt per one to three moles of a compound selected from the group consisting of gluconic acid, gluconolactone and mixtures threof.

5. The composition according to claim 6 having about one mole of m-AMSA gluconate salt per 1.5 moles of said compound.

6. A stable, solid, water-soluble composition for reconstitution with water or aqueous vehicle as a stable solution of m-AMSA, said composition being produced by the steps of
(1) forming an aqueous solution of m-AMSA and said compound selected from the group consisting of gluconic acid, gluconolactone and mixtures thereof, the molar ratio of the said compound to m-AMSA being from about 2:1 to about 4:1; and
(2) lyophilizing the so-produced aqueous solution.

7. The composition according to claim 8 wherein about 2.5 moles of said compound are used per mole of m-AMSA.

8. The composition according to claim 8 or claim 9 wherein the said compound used is gluconolactone.

9. The composition according to claim 8 wherein the aqueous solution of step (1) is formed by reacting about 5 g. m-AMSA and 6.23 g. gluconolactone per liter of solution.

10. A stable, solid, water-soluble composition for reconstitution with water or aqueous vehicle as a stable solution of m-AMSA, said composition comprising a mixture of about one mole of m-AMSA gluconate salt per 0.2 to 10 moles of a compound selected from the group consisting of gluconic acid, gluconolactone and mixtures thereof.

11. The composition according to claim 10 having about one mole of m-AMSA gluconate salt per approximately 1 to approximately 6 moles of said compound.

12. A stable, solid, water-soluble composition for reconstitution with water or aqueous vehicle as a stable solution of m-AMSA, said composition being produced by the steps of
(1) forming an aqueous solution of m-AMSA and said compound selected from the group consisting of gluconic acid, gluconolactone and mixtures thereof, the molar ratio of the organic acid to m-AMSA being from about 1.2:1 to about 11:1; and
(2) lyophilizing the so-produced aqueous solution.

13. The composition according to claim 12 wherein approximately 2 to approximately 7 moles of said compound are used per mole of m-AMSA.

14. The composition according to claim 12 wherein the compound used is gluconolactone.

15. The composition according to claim 12 wherein the aqueous solution of step (1) is formed by reacting about 7.85 g. m-AMSA and a sufficient amount of gluconolactone to produce a mole ratio of gluconolactone to m-AMSA of about 8.5:1 per liter of solution.

16. A stable, solid water-soluble composition for reconstruction with water or aqueous vehicle as a stable solution of m-AMSA, said composition comprising a mixture of about one mole of m-AMSA gluconate salt per 0.2 to 10 moles of gluconic acid.

17. The composition according to claim 16 having about one mole of m-AMSA gluconate salt per approximately 1 to approximately 6 moles of gluconic acid.

18. A stable, solid, water-soluble composition for reconstitution with water or aqueous vehicle as a stable solution of m-AMSA, said composition being produced by the steps of
(1) forming an aqueous solution of m-AMSA and gluconic acid the molar ratio of the gluconic acid to m-AMSA being from about 1.2:1 to about 11:1; and
(2) lyophilizing the so-produced aqueous solution.

19. The composition according to claim 18 wherein approximately 2 to approximately 7 moles of gluconic acid are used per mole of m-AMSA.

20. The composition according to claim 18 wherein the aqueous solution of step (1) is formed by reacting about 7.85 g. m-AMSA and about 33 g. gluconic acid per liter of solution.

21. The composition according to claim 13 wherein the compound used is gluconolactone.

* * * * *